United States Patent
Dwivedi et al.

[11] Patent Number: 6,076,522
[45] Date of Patent: Jun. 20, 2000

[54] METERING APPARATUS

[75] Inventors: Sarvajna Kumar Dwivedi, San Diego, Calif.; William Leroy Roberts, II, Apex, N.C.; Mark Joseph Sacchetti, Raleigh, N.C.; Michiel Mary Van Oort, Durham, N.C.

[73] Assignee: Glaxo Wellcome Inc., Research Triangle Park, N.C.

[21] Appl. No.: 09/180,648

[22] PCT Filed: May 22, 1997

[86] PCT No.: PCT/EP97/02594

§ 371 Date: Nov. 12, 1998

§ 102(e) Date: Nov. 12, 1998

[87] PCT Pub. No.: WO97/44080

PCT Pub. Date: Nov. 27, 1997

[30] Foreign Application Priority Data

May 23, 1996 [GB] United Kingdom .................... 9610821

[51] Int. Cl.⁷ .................................................. A61M 15/00
[52] U.S. Cl. ................................ 128/203.15; 128/203.12
[58] Field of Search ......................... 128/203.15, 203.12, 128/203.21

[56] References Cited

U.S. PATENT DOCUMENTS

| | | |
|---|---|---|
| 3,913,795 | 10/1975 | Coucher et al. . |
| 3,967,761 | 7/1976 | Melton, Jr. et al. ...................... 222/194 |
| 4,161,516 | 7/1979 | Bell . |
| 4,177,941 | 12/1979 | Leong ...................................... 222/636 |
| 4,395,421 | 7/1983 | Taylor et al. . |
| 4,533,571 | 8/1985 | Kramer et al. . |
| 4,649,911 | 3/1987 | Knight et al. ....................... 128/200.21 |
| 4,667,668 | 5/1987 | Wetterlin . |
| 4,668,218 | 5/1987 | Virtanen . |
| 4,768,314 | 9/1988 | Thomson . |
| 4,805,811 | 2/1989 | Wetterlin . |
| 5,005,769 | 4/1991 | Sauvinet et al. . |
| 5,213,817 | 5/1993 | Pelley . |
| 5,350,597 | 9/1994 | Pelley . |
| 5,368,237 | 11/1994 | Fulkerson . |
| 5,520,735 | 5/1996 | Mulder . |
| 5,571,323 | 11/1996 | Duffy et al. . |
| 5,876,754 | 3/1999 | Wunderlich et al. .................... 424/489 |

FOREIGN PATENT DOCUMENTS

| | | |
|---|---|---|
| 0 211 595 | 2/1987 | European Pat. Off. . |
| 0 455 463 A1 | 11/1991 | European Pat. Off. . |
| 0 467 172 A1 | 1/1992 | European Pat. Off. . |
| 2598918 | 5/1986 | France ............................... 128/203.15 |
| 3607187 A1 | 5/1986 | Germany ........................... 128/203.15 |
| WO 92/00115 | 1/1992 | WIPO . |
| WO 94/20164 | 9/1994 | WIPO . |

OTHER PUBLICATIONS

Principles of Operation Brochure, FMI.

*Primary Examiner*—Aaron J. Lewis
*Assistant Examiner*—Teena Mitchell
*Attorney, Agent, or Firm*—James P. Riek

[57] ABSTRACT

An apparatus (100) adapted for applying to a carrier (C) a suspension (S) comprising a suspending agent and a powdered medicament. The apparatus (110) includes a reservoir (110), a junction container (120) adapted to contain a liquid, an outlet line (130) extending from the reservoir (110) and through the junction container (120) to a pump (P), a nozzle (160) connected to the pump (P) and a sonicator (150) operatively connected to the junction container (120). The reservoir (110) is adapted to maintain the agent and the medicament admixed in suspension. The nozzle (160) is formed from an inner cylinder (161) disposed within an outer cylinder (162), thereby defining a space (X) therebetween, and includes a purge line (165) fluidly connected with the outer cylinder (162) for providing a gas jet to the space (X). The sonicator (150) creates waves in the liquid in the container (110) to help prevent the suspension (S) from flocculating as it travels through the outlet line (130) from the reservoir (110) and to the pump (P). The pump (P) expels the suspension (S) through the nozzle (160) to the carrier (C), and a gas jet (GJ) from the purge line (165) prevents capillary forces from allowing the suspension (S) to collect around the tip (T) of the inner cylinder (161) of the nozzle (160).

30 Claims, 5 Drawing Sheets

METERING APPARATUS

FIELD OF THE INVENTION

The present invention relates, in general, to an apparatus for applying powdered medicament to a carrier, with the carrier being adapted for dosing of the medicament to a patient. More particularly, the present invention relates to a metering apparatus for dispensing a suspension of a suspending agent and one or more doses of dry powdered medicament onto a carrier (for instance, a carrier screen adapted to be positioned within a dry powder inhalator for dosing of the medicament to a patient), after which the suspending agent evaporates thereby leaving dry powder particles on the carrier.

RELATED ART

Two respiratory disease treatments involving inhalation of an appropriate medicament into the lungs to ease patient breathing and increase air capacity are widely used. One is inhalation of a medicament from a drug solution or suspension in an aerosol container (i.e., a pressurized container) using a gas propellant, such as a chlorofluorocarbon. The other is inhalation of a dry powdered medicament (generally admixed with an excipient for instance, to enable dispensing microgram quantities of medicament) from a dry powder inhalator.

Not only do various dry powder inhalator devices exist for dosing of fine particulate powdered medicaments to the respiratory tract of a patient, but also several apparatus exist for loading the powder into the device. The dose employed with such dry powder inhalators is usually about 50 to about 500 $\mu$g of medicament and about 500 to about 25,000 $\mu$g of excipient. The powdered particles contained in the inhalator usually are micronized, typically having a particle size of <10 $\mu$m, more preferably <6 $\mu$m, even more preferably <5 $\mu$m, which is an appropriate size so that the particles can be drawn into the lungs. These inhalators employ capsules, blisters, velvet fibers, screens, and the like, loaded with powdered medicament as further explained below.

For instance, one such dry powder inhalator device is disclosed in PCT Published Application No. WO 92/00115, published Jan. 9, 1992, to Gupte et al., which shows a velour-fiber or velvet-fiber carrier material loaded with medicament powder between the fibers. During use, an air stream lifts powder from the carrier to entrain the powder within the air stream which is then inhaled by the patient. The powder may be loaded between the fibers from droplets of a suspension of the powder and a suspending agent (such as dichloromethane) and located on the carrier material such that when dispensed from a metering device, each droplet is at the requisite distance from the next droplet.

The metering device disclosed in PCT Published Application No. WO 92/00115 includes a first storage container for the suspension, from which it flows through a first pipe to a magnetic valve containing a piston and then laterally past the valve surfaces and piston through a second pipe and into a second storage container. The valve is associated with a third pipe from which the suspension is applied to the carrier by employing an electromagnet to withdraw the piston and free the opening to the third pipe, thereby enabling the suspension to reach the carrier. Each of the first and second storage containers is fitted with an agitator to keep the medicament powder particles constantly in suspension.

Also of interest is another inhalator device that utilizes hard gelatin capsules each carrying a load of powdered medicament and possibly also various excipients. A capsule is inserted into an inhalator and perforated so that the patient can generate an air stream on the mouthpiece of the inhalator and inhale the powder. Dry powder inhalators using this capsule technology are disclosed in U.S. Pat. No. 4,161,516 to Bell and U.S. Pat. No. 4,395,421 to Taylor et al., which show, respectively, an agglomerator-pelletizer apparatus and a wet granulator apparatus for preparing pellets or granules of the asthma medicament, disodium cromoglycate, for loading inside of a capsule.

Another type of inhalator device contains a package insert having a number of spaced-apart plastic blisters, each carrying a metered dose of powdered medicament. As the patient moves each blister into position, the patient employs a mechanism in the device to break the blister, releasing the powder for inhalation. This type of inhalator is disclosed in European Published Patent Application Nos. 0 211 595 A2 to Newell et al., 0 455 463 A1 to Velasquez et al., and 0 467 172 A1 to Cocozza et al.

A relatively new carrier for use with a dry powder inhalator is described in PCT Published Application No. WO 94/20164, published Sep. 15, 1994, to Mulhauser et al. A dose of powdered asthma medicament, such as salmeterol hydroxynapthoate, is impregnated and compacted into each of several spaced interstices along the circumference of a carrier screen disc. During inhalation, air impinging on the screen interstices surrounds each impregnated dose, detaching and entraining it prior to deposition in the patient's lungs.

An improvement over the carrier screen disclosed in PCT Published Application No. WO 94/20164 is described in U.S. Pat. No. 5,503,869 and U.S. patent application Ser. No. 08/328,578 (both to Van Oort), the disclosures of which are incorporated herein by reference. These two applications describe a medicament carrier which is adapted for use in a dry powder inhalator device and includes one or more carrier screens having carrier surfaces that define a plurality of interstices in the screen. At least one or more doses of powdered medicament are loaded onto the screen surfaces whereby the screen interstices are at least partially open and free of the powdered medicament. Since the medicament dose is not impregnated into the interstices and thus is not dependent on the interstitial void volume of the carrier screen, much greater flexibility in medicament dose range with a specific carrier screen interstice size is provided.

For loading the powder onto the screen surfaces in accordance with the disclosures of U.S. Pat. No. 5,503,869 and U.S. patent application Ser. No. 08/328,578, a selected amount of the powder (such as 50 $\mu$g) is admixed with a suspending agent (such as perfluoropentane). The resultant suspension is dispensed from a metering device onto the carrier screen, after which the suspending agent evaporates and leaves microfine dry powder particles on the screen surfaces. Typically, to facilitate metering, 6 carrier screens are secured in a screen holder assembly, and then for use in an inhalator, the 6 loaded carrier screens (colloquially referred to as drug "dots") are placed in a twin screen assembly together with 6 respective second or top impaction screens. The impaction screen is the screen on which the medicament impinges when it is entrained by air. Thereafter, it is dispersed into the patient's lungs. Representative screens (both the carrier screens and the impaction screens) are in the form of a mesh and usually made of a screen material including, but not limited to, polypropylene, copolymer of ethylene chlorotrifluoroethylene, copolymer of ethylene tetrafluoroethylene, or stainless steel (hereinafter, abbreviated as PP, E-CTFE, ETFE, and SS, respectively).

SUMMARY OF THE INVENTION

In accordance with the present invention, provided is an apparatus adapted for applying to a carrier a suspension comprising a suspending agent and one or more doses of a powdered medicament, after which the suspending agent is evaporated off leaving the powdered medicament applied to the carrier. The apparatus comprises a reservoir, an outlet line, a pump, and a concentric nozzle.

The reservoir has a top and a bottom, and is adapted for maintaining the suspending agent and the dry powdered medicament admixed in suspension. The outlet line is in fluid communication with the reservoir, and as further described below, in fluid communication with the piston of the pump, so that the suspension may travel through the outlet line from the reservoir to the pump.

The concentric nozzle has a top and a bottom, and is formed from an inner cylinder disposed within an outer cylinder, thereby defining a space therebetween. The inner cylinder terminates in a tip disposed near and preferably extending beyond the nozzle bottom. Also, the nozzle has a purge line fluidly connected with the outer cylinder for providing a gas jet to the space.

The pump has a piston and associated cylinder that are fluidly connected with the outlet line, and also operatively associated with the nozzle, so that the suspension may travel from the outlet line into the piston cylinder and the piston cylinder may be filled with a selected amount of the suspension. In particular, the selected amount should contain one dose of the powdered medicament and the powdered medicament should be a dry powdered medicament. As a result, one stroke provided by the pump will expel the selected amount of the suspension out of piston cylinder and through the inner cylinder of the nozzle to the carrier, and a gas jet provided from the purge line to the space between the inner and outer cylinder, will prevent capillary forces from allowing the selected amount of the suspension, as it is expelled, from collecting around the tip of the inner cylinder. In particular, the gas jet should be provided concurrently together with the stroke.

In one embodiment, the apparatus further includes a junction container and a sonicator. The use of the junction container and sonicator will depend on flocculation characteristics of the particular medicament and suspending agent.

The junction container has a top and a bottom, and is adapted for containing a liquid. The outlet line, which is in fluid communication with the reservoir, passes from the reservoir and then enters and Exits the junction container to allow the suspension to travel by way of the outlet line through the junction container.

The sonicator is operatively associated with the junction container, whereby when the junction container contains liquid and the sonicator is activated, the sonicator creates waves in the liquid in communication with the outlet line and thereby prevents the suspension traveling through the outlet line from forming floccules that could agglomerate together and clog the outlet line. Thus, in this embodiment, the piston and associated cylinder are fluidly connected with the outlet line where the outlet line exits the junction container, and the suspension travels through the outlet line from where the outlet line exits the junction container to where the outlet line is fluidly connected with the piston cylinder, and thus, the piston cylinder may be filled with a selected amount of the suspension, as described above.

It is therefore the object of the present invention to provide an apparatus for metering a suspension of a suspending agent and at least one dose of powdered medicament to a carrier.

It is an advantage of the apparatus of the present invention that more uniform aliquots of the suspension can be metered to the carrier than can be accomplished with prior art metering apparatus.

Some of the objects and advantages of the invention having been stated, other objects will become evident as the description proceeds, when taken in connection with the accompanying drawings and Examples described below.

DETAILED DESCRIPTION OF THE INVENTION

It is noted that in the drawings, like numerals indicate like elements throughout.

Figure 1:
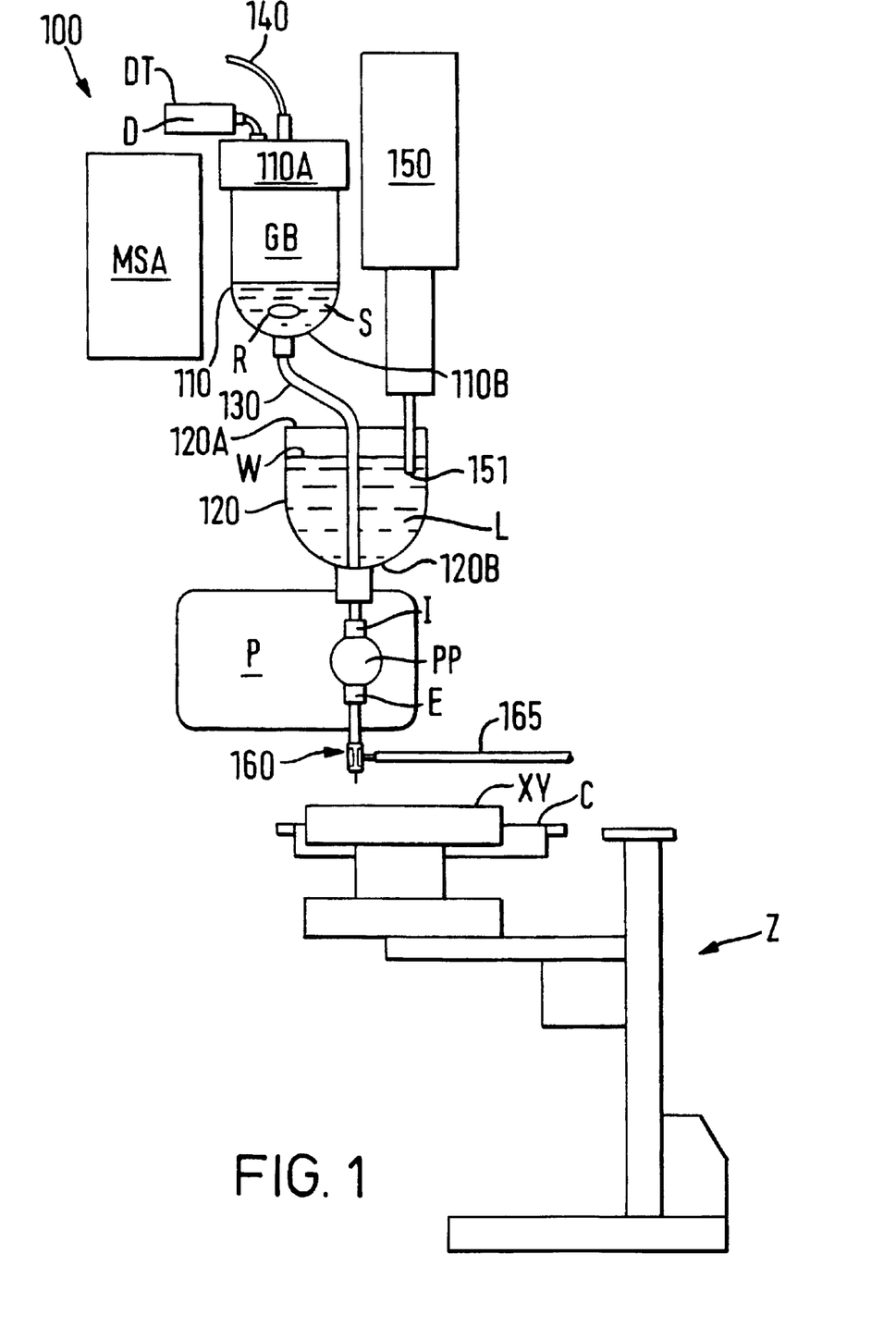
FIG. 1 is a schematic view of the metering apparatus of the present invention.

Referring now to FIG. 1, illustrated is a schematic view of a particular embodiment of metering apparatus 100 which forms the subject of the instant invention. Apparatus 100 is adapted for applying suspension S comprising a suspending agent and one or more doses of a powdered medicament, particularly a dry powdered medicament, to a carrier, which, for ease of application of suspension S, may be held in a suitable holder therefor, schematically shown as carrier/holder C. Various excipients well known to those skilled in the art may be present in suspension S. For convenience, carrier/holder C is simply referred to hereinafter as carrier C.

For maintaining stability of carrier C during application of suspension S thereto, carrier C may conveniently be retained in horizontal stage or brace XY, which is attached to vertical stage or brace Z. Also, positioning system (not illustrated) may be provided for maintaining apparatus 100 in place over carrier C during application of suspension S to carrier C, particularly in a factory production setting, where a plurality of carriers C is moving on an assembly line, and as the line is stopped, a positioning system is needed to hold apparatus 100 in place and/or to hold a particular carrier C in place so that apparatus 100 is properly aligned over the particular carrier C as suspension S is dispensed from apparatus 100 to the particular carrier C. Such positioning systems are well known to those skilled in the art. After application of suspension S, the suspending agent is evaporated, such as by the ambient temperature of the air, by reduced pressure, or by providing heat, leaving powdered medicament deposited on carrier C.

Apparatus 100 includes reservoir 110 having top 110A and bottom 110B. Reservoir 110 is adapted for holding and mixing a suspending agent and a powdered medicament so that they may be maintained admixed as suspension S.

For instance, suitable portions of a suspending agent and a powdered medicament, respectively, are measured out. Then, they are placed (suitably, the powdered medicament first and the suspending agent second) into a vial (not shown) and mixed. Top 110A is opened, and the contents of the vial are poured into reservoir 110, and top 110A is closed. Alternatively, the measured out portions are poured (suitably, the powdered medicament first and the suspending agent second) directly into reservoir 110.

A particular quantity of medicament contained in selected amount of suspension SAS may be one dose, less than one dose, or more than one dose. However, a suitable volume of suspension S containing suitable measured quantities should be chosen with a proper ratio of suspending agent to powdered medicament so that during application of suspension S to carrier C, a selected amount of suspension SAS will be dispensed, as further described below, particularly to provide one dose of the medicament to carrier C. Nevertheless, if desired, as described below in the Example vis-a-vis dispensing of fluticasone propionate onto an ETFE carrier screen, one dispensing of a particular quantity of selected amount of suspension SAS to one location on carrier C can be a portion of the desired dose, and thus, dispensing of selected amount of suspension SAS can be repeated 2 times, 3 times, or more, till the amount of suspension S on carrier C is one dose of medicament. Moreover, it is to be understood that a dose can vary so that an amount that is a dose for a first type of medicinal administration to a first type of patient may be a smaller amount, i.e., a portion of a dose, for a second type of medicinal administration to a second type of patient who has a more severe case of the same medical condition as the first type of patient.

Usually, the volume of selected amount of suspension SAS that is dispensed is about 1 μl to about 5 μl, and hence, apparatus 100 is especially suitable as a micro volume metering apparatus. Also, if the medicament is intended for inhalation, then, the medicament should be chosen of the appropriate particulate particle size, typically, a size <10 μm, more particularly <6 μm, even more particularly <5 μm, so that the particles can be drawn into the lungs.

Various suspending agents and powdered medicaments may be employed. The suspending agent may include, but is not limited to, various organic agents and/or inorganic agents. Organic agents may include, but are not limited to, fluorinated hydrocarbons, chlorinated hydrocarbons, and/or hydrocarbons, such as perfluoromethylcyclohexane (hereinafter, abbreviated as PFMCH), perfluorohexane, perfluoropentane, dichloromethane, hexane, and combinations thereof. Inorganic agents include, but are not limited to, carbon dioxide and sulfur hexafluoride.

The respirable powdered medicaments for inhalation therapy or systemic absorption via the respiratory tract to treat respiratory disorders such as asthma, bronchitis, chronic obstructive pulmonary diseases and chest infection may be selected from, but not limited to, the group consisting, for example, analgesics, e.g., codeine, dihydromorphine, ergotamine, fentanyl or morphine; anginal preparations, e.g. diltiazem; antiallergics, e.g. cromoglycate, ketotifen or neodocromil; antiinfectives e.g. cephalosporins, penicillins, stretomycin, sulphonamides, tetracyclines and pentamidine; antihistamines, e.g. methapyrilene; anti-inflammatories, e.g. fluticasone propionate, beclomethasone dipropionate, flunisolide, budesonide or triamcinolone acetonide; antitussives, e.g. noscapine; bronchodilators, e.g. salmeterol, salmbutamol, ephedrine, adrenaline, fenoterol, formoterol, isoprenaline, metaproterenol, phenylephrine, phenylpropanolamine, pirbuterol, reproterol, rimiterol, isoetharine, terbutaline, tulobuterol, orciprenaline, or (−)-4-amino-3,5-dichloro-α-[[[6-[2-(2-pyridinyl)ethoxy]hexyl]amino]methyl] benzenemethanol; diuretics, e.g. amiloride; anticholinergics, e.g. ipratropium, atropine, oxitropium; hormones, e.g., cortisone, hydrocortisone or prednisolone; xanthines e.g. aminophylline, choline theophyllinate, lysine theophyllinate or theophylline and therapeutic proteins and peptides, e.g. insulin or glucagon. Additional medicaments include isoproterenol, metaprotarenol, pirbuterol, triacetonide, bambuterol, and mometasone. Further medicaments may be selected from any other suitable drug useful in inhalation therapy. It will be clear to a person skilled in the art that, where appropriate, the medicaments may be used in the form of salts (e.g. as alkali metal or amine salts or as acids addition salts) or as esters (e.g. lower alkyl esters) or as solvates (e.g. hydrates) to optimise the activity and/or stability of the medicament. Preferred medicaments are salbutamol, salmeterol, fluticasone propionate, beclomethasone dipropionate, terbutaline, cromoglycate, budesonide, and triamcinolone acetonide and/or salts thereof.

The medicament may, when deemed advantageous, include a suitable excipient acceptable for inhalation into the human body, which may be selected from organic excipients, such as polysaccharides (i.e., starch, cellulose, and the like), lactose, glucose, mannitol, amino acids, and maltodextrins, or may be inorganic excipients, such as calcium carbonate and sodium chloride. The excipient may be included with the medicament via well known methods, such as by admixing, co-precipitating, and the like.

For any particular powdered medicament, the suspending agent employed should ideally have a density approximately the same as the true density of the powdered medicament. For instance, with fluticasone propionate as the medicament, particularly used is a blend of PFMCH and hexane as the suspending agent, more particularly, 2.5% weight/volume fluticasone propionate is admixed with a blend of 70% by volume PFMCH and 30% by volume hexane.

Although the particular carrier C employed in the Laboratory Examples below was a representative mesh screen (such as disclosed in the above-mentioned U.S. Pat. No. 5,503,869, and U.S. patent application Ser. No. 8/328,578 which describe medicament carrier screens that have powdered medicament on the carrier screen surfaces and that are adapted for use in a powder inhalator device), it is not intended to limit the invention such that carrier C is a mesh screen or the medicament is for inhalation. In addition to the particular uses of apparatus 100 for applying selected amount of suspension SAS onto the carrier surfaces of such screens useful in powder inhalators, apparatus 100 may advantageously be employed to meter medicament into or onto various other carriers C, such as, but not limited to, gelatin capsules or caplets, into plastic blisters, into medicine vials, between fibers (such as velvet fibers), into carrier interstices (such as described in PCT Published Application No. WO 94/20164), onto a tablet for the excipient coating thereof, onto the barrel of a syringe, and the like, all of which other carriers C are well known to those skilled in the art.

Hence, by phrases such as "apparatus 100 is adapted for applying suspension S to carrier C", "apparatus 100 is adapted for applying selected amount of suspension SAS to carrier C", and the like, it is intended to include into, within, or onto carrier C, as the case may be, depending on the particular type of carrier C, medicament, and/or suspending agent being used.

Mixing inside of reservoir 110 may be accomplished via any suitable agitator device, one example being a mechanical stirring apparatus affixed therein, for instance a paddle wheel (not shown) for stirring, and another example being magnetic stirring apparatus MSA. For instance, by placing magnetic stirring rod R in suspension S and locating magnetic stirring apparatus MSA close to reservoir 110, then, when magnetic stirring apparatus MSA is activated, rod R will spin and thereby mix medicament and suspending agent so that they are maintained as suspension S.

In one embodiment, apparatus 100 may include junction container 120, having top 120A and bottom 120B, and adapted for containing liquid L such as water. In this embodiment in which apparatus 100 includes junction container 120, then, apparatus 100 may also include sonicator 150, which is described further below.

Further included as part of apparatus 100 is outlet line 130, such as a hollow flexible tube (for instance, TEFZEL brand tubing available from Optimize Technologies, Inc., Portland, Oreg., USA), in fluid communication with reservoir 110. Outlet line 130 passes from reservoir 110, and when junction container 120 is present, outlet line 130 then enters and exits junction container 120 to allow suspension S to travel via outlet line 130 through junction container 120 and (when liquid L is present in junction container 120) through liquid L.

Particularly, apparatus 100 may include gas line 140 fluidly connected to reservoir 110 and adapted for providing gas blanket GB, such as a blanket of nitrogen or any other appropriate inert gas, in reservoir 110 on top of suspension S. For supplying nitrogen, gas line 140 is connected to a conventional pressurized tank (not shown) containing nitrogen and having a regulator valve (not shown) for line 140. A suitable pressure for gas blanket GB on suspension S is 0 to 20 psig (0 to 0.24 MPa), particularly 15 psig (0.20 MPa). The gas blanket GB help purge reservoir 110 of residual moisture and oxygen to create an inert atmosphere during stirring. Depending on the pump configuration used, the gas blanket GB can help to move suspension S into outlet line 130. Preferably however, gas blanket GB is at atmospheric pressure.

Furthermore, it is desirable to have drying tube DT, containing a conventional desiccant D, such as calcium chloride or calcium sulfate, attached to reservoir 110 and fluidly connected therewith, to help keep moisture out of suspension S, as many medicaments readily attract moisture that can cause capillary adhesion to the reservoir walls or in nozzle 160 (which is undesirable during loading of carrier C). When drying tube DT is present, gas blanket GB probably does not help to move suspension S into outlet line 130, since drying tube DT communicates with the atmosphere.

In the embodiment in which apparatus 100 includes junction container 120 (as described above) and sonicator 150, sonicator 150 has probe end 151. When liquid L, such as water or other suitable coupling media, is present in junction container 120 and probe end 151 is disposed in liquid L and sonicator 150 is activated, sonicator 150 creates pressure waves W in liquid L. Pressure waves W contact outlet line 130 and thereby prevent powdered medicament in the suspension S traveling through outlet line 130 from agglomerating into large floccules that are undesirable and could clog outlet line 130.

Accordingly, for convenience, apparatus 100 may be provided with optional junction container 120 and sonicator 150, and if the flocculation characteristics of the particular medicament and suspending agent are not problematic, sonicator 150 can be left turned off and junction container 120 left empty of liquid L. That way, should the need arise for when apparatus 100 is used with other medicaments and suspending agents that would create flocculation and clogging, junction container 120 and sonicator 150 are already present so that junction container 120 may be filled with liquid L and sonicator 150 turned on.

Apparatus 100 further includes concentric nozzle 160 (better seen in the enlarged view in FIG. 2) having top 160A and bottom 160B. Nozzle 160 is formed from hollow inner cylinder 161 having inside hollow space passageway 161A and being disposed within hollow outer cylinder 162. Thus, inner cylinder 161 and outer cylinder 162 define open space X therebetween. Nozzle 160 further includes nozzle inlet 163 leading to hollow space 161A of inner cylinder 161.

Hollow passageway 161A and inlet 163 should both be particularly of generally circular cross-section, and may have the same inner diameter or one may have a larger inner diameter than the other. Generally, passageway 161A should have a larger inner diameter than inlet 163. Suitable inner diameters for both of hollow passageway 161A and inlet 163 range from about 0.01 to about 0.035 inch (about 0.0254 to about 0.0889 cm), and suitably hollow passageway 161A has an inner diameter of about 0.016 inch (about 0.041 cm) and inlet 163 has an inner diameter of about 0.02 inch (about 0.050 cm).

Inner cylinder 161 terminates in outlet tip T near and preferably, as shown in the Figures, extending beyond bottom 160B. Tip T may suitably be provided with an inside diameter from about 0.010 inch to about 0.035 inch (about 0.0254 cm to about 0.0889 cm), more particularly about 0.016 inch to about 0.030 inch (about 0.041 cm to about 0.076 cm). For instance, when suspension S comprises fluticasone propionate as the medicament and a blend of hexane and PFMCH as the suspending agent, then tip T may be provided with an inside diameter of about 0.016 inch (about 0.041 cm). The distance between tip T and bottom 160B is adjustable for different suspensions. For instance, a suitable distance is 3.4 mm. For when suspension S comprises 2.5% fluticasone propionate in PFMCH.

Fluidly connected to outer cylinder 162 is gas purge line 165 for providing gas jet GJ, such as a jet of nitrogen, to space X and over tip T. Gas purge line 165 should be at an angle of 90° to nozzle 160 for optimization of gas flow characteristics. The inner wall of outer cylinder 162 may optionally have vanes (not shown) attached to it to assist in directing gas jet GJ. Further to ensure a tight fit for when gas jet GJ is provided over tip T, outer cylinder 162 may be wrapped with sleeve or jacket (not shown), such as a ribbon of tape. For supplying gas, such as nitrogen or another inert gas, gas purge line 165 is connected to a conventional pressurized tank (not shown) containing nitrogen and having a regulator valve (not shown) for purge line 165. The tank may be the same as is used to supply gas line 140 mentioned above.

Between junction container 120 and concentric nozzle 160 apparatus 100 includes pump P (see FIG. 1), having pump piston and associated cylinder PP with piston inlet I and piston exit E. A suitable pump is commercially available from Fluid Metering Incorporated, Oyster Bay, N.Y., USA as Item No. QC 72, with adapter RH/Q and with assembly RHOOCKCLF including a pump-head, a piston, a liner (i.e., a bore or cylinder surrounding the piston), and a pump dial for setting the stroke volume of the piston as it moves within its cylinder. The particular piston of this FMI (Fluid Metering Incorporated, Oyster Bay, N.Y., USA) pump is generally of a solid cylindrical shape (but missing a quarter solid section thereof, the void space defined by the missing section being of generally hemi-cylindrical shape). Moreover, this particular piston is adapted for rotating 360°, as well as being adapted for longitudinal movement (i.e., the piston stroke action), which movement of the piston within the piston cylinder is adjusted by setting the dial.

Outlet line 130 from junction container 120 is connected fluidly at inlet I to pump piston and associated cylinder PP of pump P. Also, via pump piston/cylinder PP at exit E, pump P is connected fluidly to concentric nozzle 160. Particularly, pump piston/cylinder PP is connected at inlet I and at exit E so that pump piston/cylinder PP is disposed horizontally and the longitudinal movement of the piston is back and forth in one direction and then in the other opposite direction in the piston cylinder (rather than pump piston/cylinder PP being disposed vertically for movement up and down of the piston in the piston cylinder).

Hence, via pump P and its pump piston/cylinder PP, nozzle 160 at its top 160A is in fluid communication with outlet line 130 where it exits junction container 120 at its bottom 120A, so that suspension S may travel into the piston cylinder, and then into nozzle inlet 163 and through hollow passageway 161A of inner cylinder 161. Therefore, selected amount of suspension SAS can pass out of inner cylinder 161 as droplet DL (see FIG. 2).

More particularly, when the piston rotates 1800, and then, moves longitudinally in one direction, suspension S enters through inlet I, filling the piston cylinder, i.e., filling the hemi-cylindrically shaped void, with selected amount of suspension SAS, which is retained within the void due to the piston being surrounded by the piston cylinder.

Figure 2:
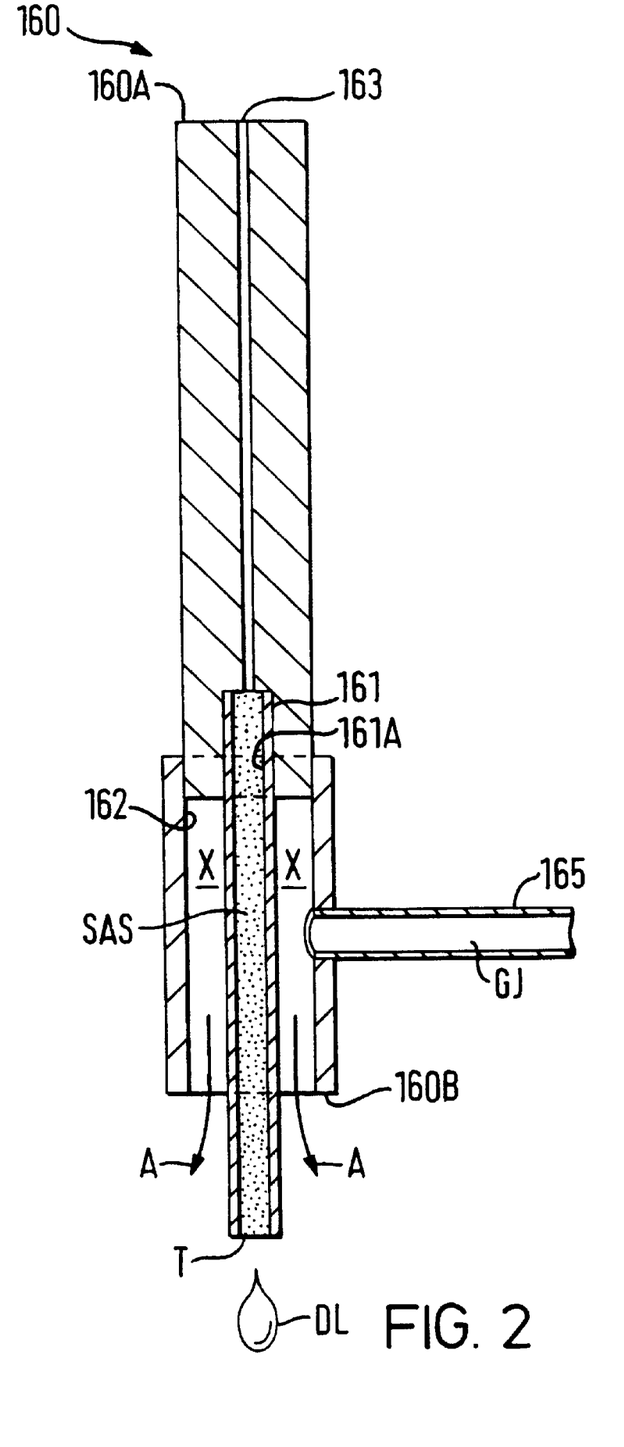
FIG. 2 is an enlarged schematic view of the concentric nozzle component of the metering apparatus illustrated in FIG. 1.

Next, in order to align the void with nozzle inlet 163, the piston rotates another 180°, and moves longitudinally in the opposite direction. One stroke in the opposite direction allows selected amount of suspension SAS to leave the piston cylinder, i.e., to leave the void, by passing out of exit E, and then passing through inner cylinder 161 and out tip T as droplet DL. Pump piston/cylinder PP should be suitably sized, for instance, with the hemi-cylindrically shaped void being precision milled to have an adjustable volume of about 0 µl to about 25 µl, more particularly about 0.3 µl to about 20 µl, even more particularly about 0.5 µl to about 20 µl, more particularly about 1 µl to about 2 µl, so that selected amount suspension SAS which pump piston PP holds preferably contains one dose of the medicament.

As a result, one longitudinal stroke of the piston, or the equivalent 360° rotation of the piston, provided by pump P will expel selected amount of suspension SAS out of the hemi-cylindrically shaped void and through hollow 161A of inner cylinder 161 and out tip T as droplet DL onto carrier C. Also, gas jet GJ is provided from purge line 165 preferably concurrently together with the stroke of the piston provided by pump P. Suitably, gas jet GJ is running continuously, but, in the alternative, may pulsate with the stroke provided by pump P. Thus, it is intended that the phrase "a gas jet is provided concurrently together with a stroke" includes either situation.

Since gas jet GJ travels in the direction of arrows A (see FIG. 2) over tip T of inner cylinder 161, gas jet GJ will help prevent capillary forces from allowing selected amount of suspension SAS, as it is expelled, from collecting around tip T during expulsion so that droplet DL is applied to carrier C. The distance between tip T and carrier C should be at least 0.001 inch (0.00254 cm), and particularly, between about 0.002 inch and 0.005 inch (about 0.0051 cm and 0.0127 cm), although tip T and carrier C may touch.

Figure 3A:
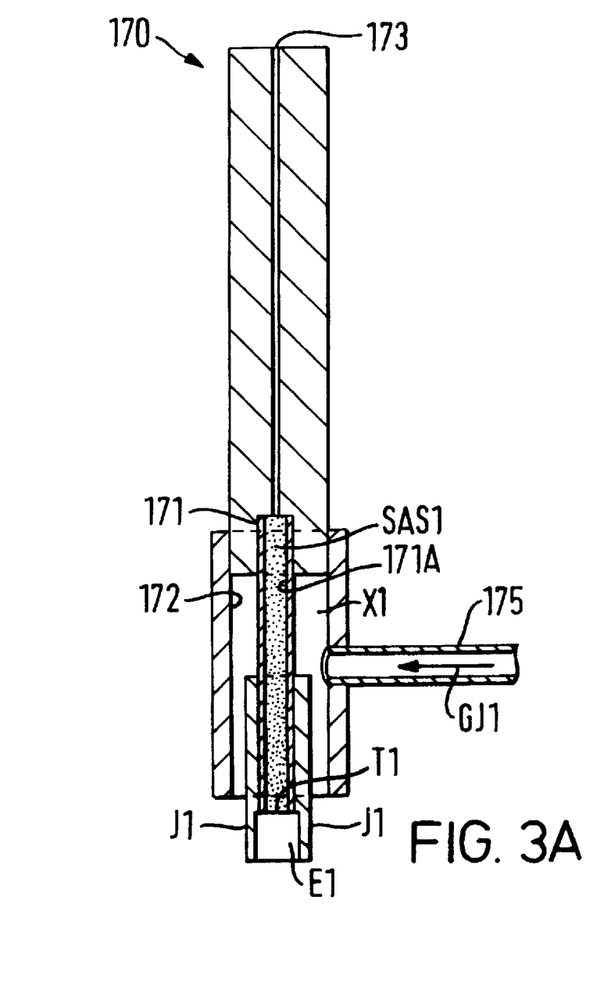
FIGS. 3A and 3B are enlarged schematic views of two alternative concentric nozzles for use in a metering apparatus in accordance with the present invention.
Figure 3B:
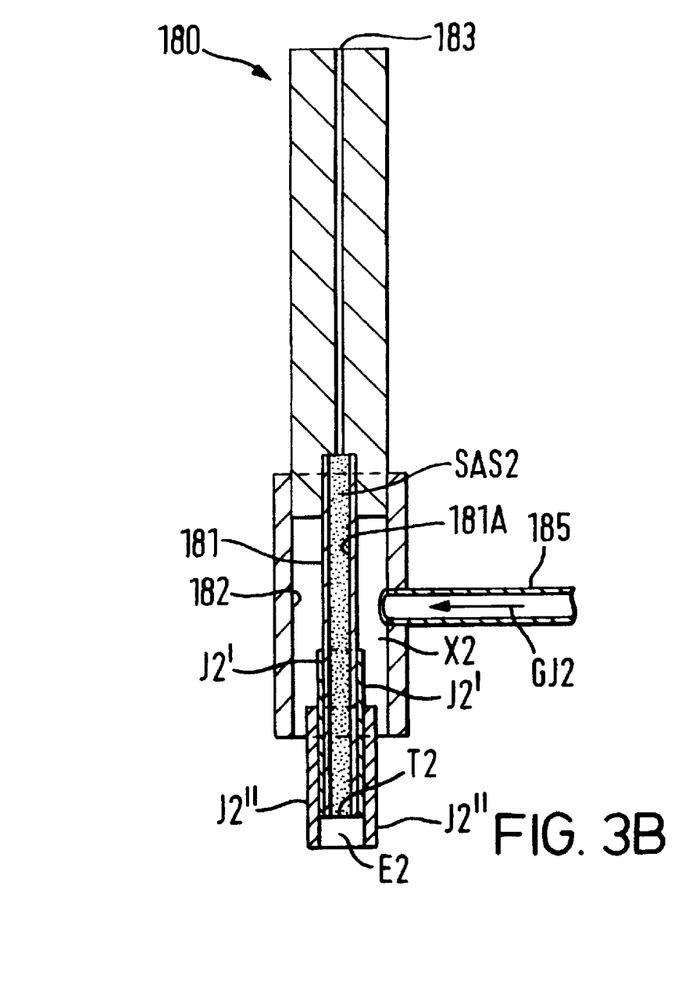

Turning now to FIGS. 3A and 3B, shown are enlarged schematic views of respective concentric nozzles 170,180, for use with metering apparatus 100 in accordance with two alternative embodiments of the present invention. Nozzles 170,180 are generally similar to nozzle 160 and respectively include the following comparable components: inner cylinders 171,181 with hollow spaces 171A,181A for dispensing selected amounts of suspension SAS1,SAS2; outer cylinders 172,182; inlets 173,183; purge lines 175,185 for gas jets (GJ1,GJ2; and jackets (not shown).

However, although inner cylinders 171,181 terminate in respective outlet tips T1,T2, the construction of outlet tips T1,T2 is different from that of outlet tip T of nozzle 160. More specifically, tip T1 cf nozzle 170 is extended vertically with discrete void extended portion E1 secured to tip T1 by sleeve or jacket J1. Particularly, extension E1 should be of 1 microliter in volume and should have an internal diameter of 0.02 inch (0.051 cm). Tip T2 of nozzle 180 is extended both horizontally and vertically with discrete void extended portion E2 secured to tip T2 by inner sleeve or jacket J2' and outer sleeve or jacket J2". Particularly, extension E2 should be of 1 microliter in volume and should have an internal diameter of 0.03 inch (0.076 cm).

Extensions E1,E2 assist respective gas jets GJ1,GJ2 in preventing capillary forces from allowing respective selected amounts of suspension SAS1,SAS2, during expulsion, from collecting around respective tips T1,T2 of respective inner cylinders 171,181.

If desired, additional functionality (not illustrated) may be incorporated onto one or more of nozzles 160,170,180 to remove any obstructions that may be present at tips T1,T2, T3, respectively.

Figure 4:
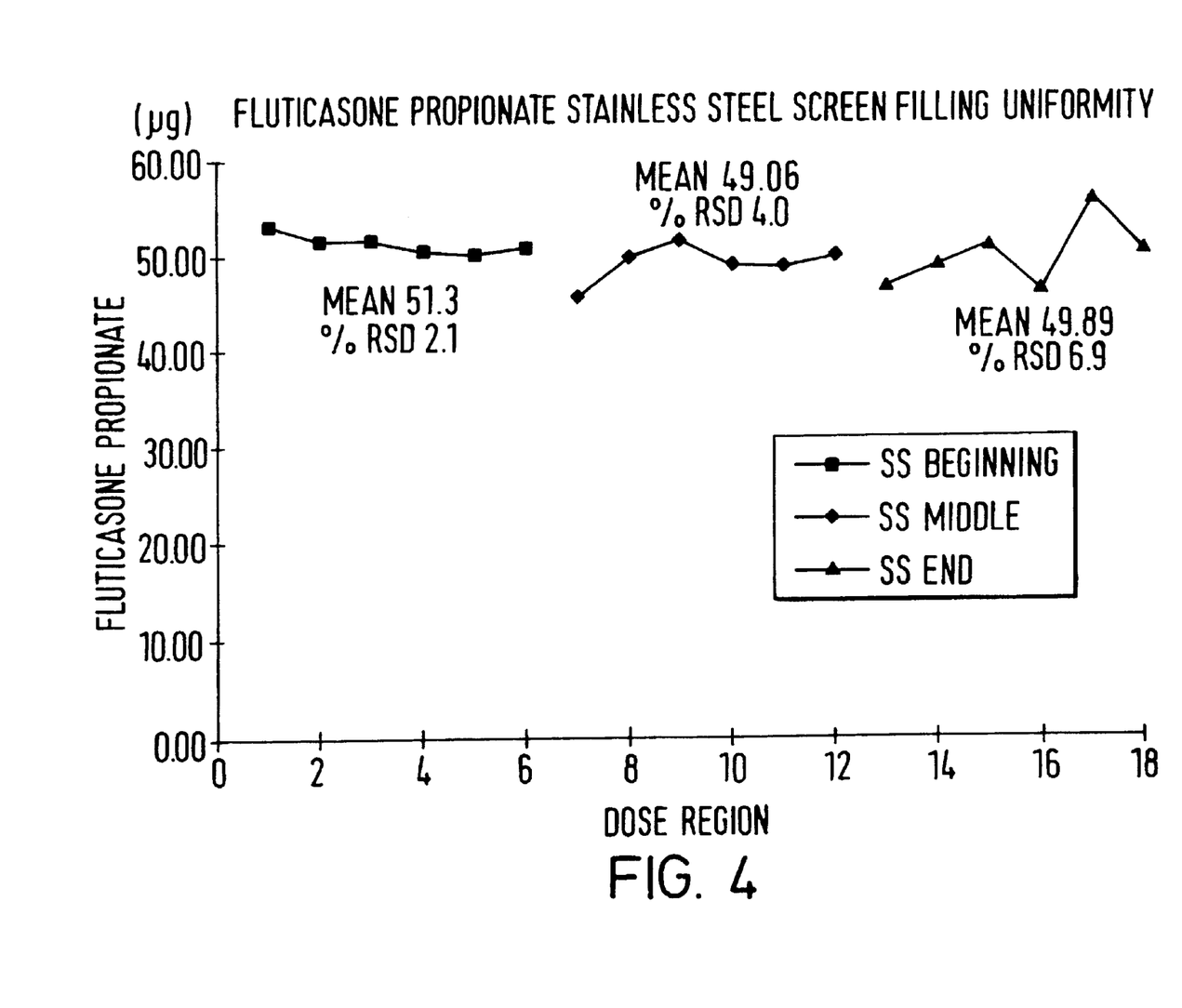
FIG. 4 is a graph illustrating the uniformity of several doses of a medicament, individually dispensed onto SS carrier screens from a suspension of the medicament and a suspending agent using the inventive metering apparatus.
Figure 5:
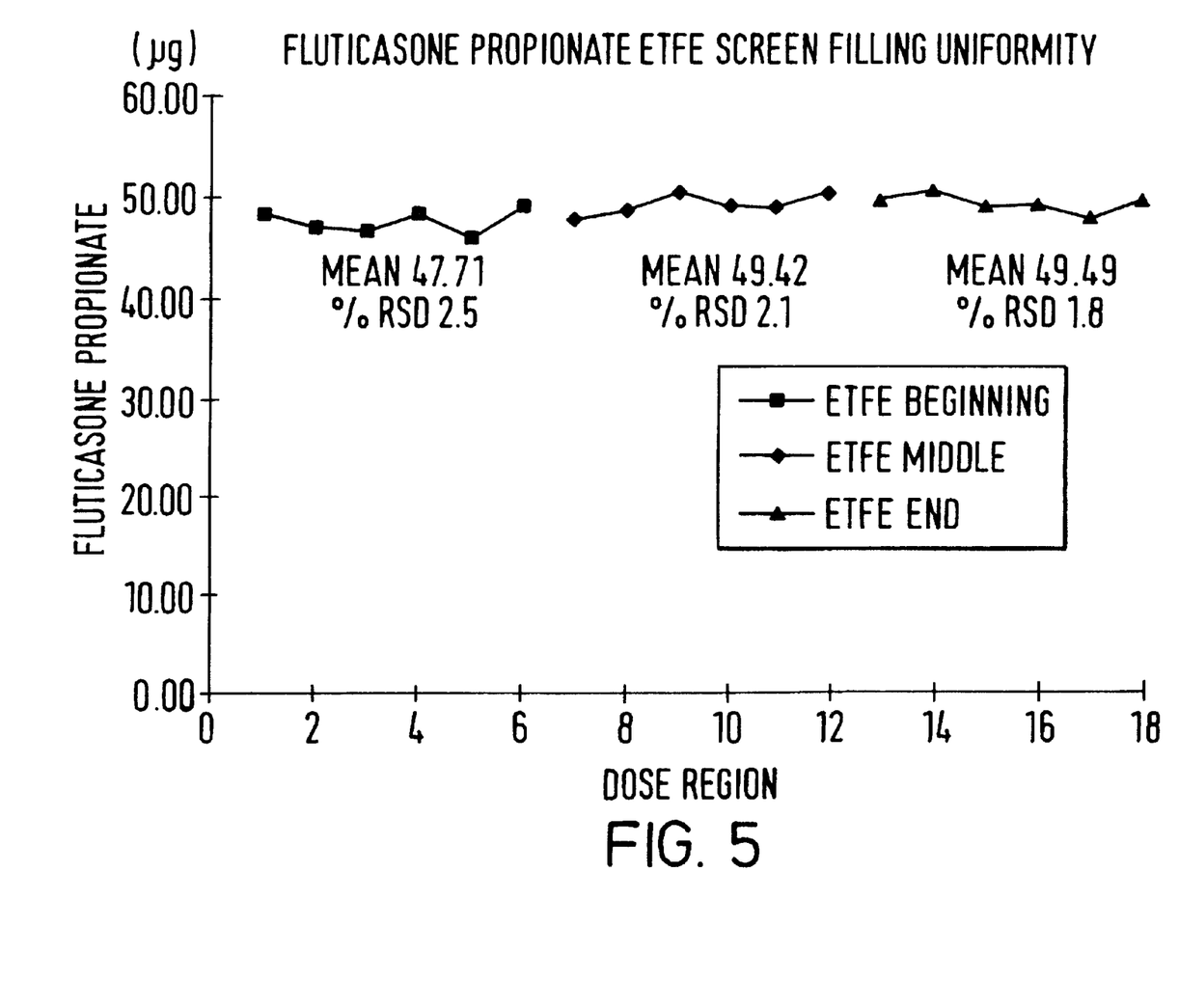
FIG. 5 is a graph illustrating the uniformity of several doses of a medicament, individually dispensed onto ETFE carrier screens from a suspension of the medicament and a suspending agent using the inventive metering apparatus.

Turning now to FIGS. 4 and 5, each represents a graph illustrating the uniformity of medicament doses on carriers when employing inventive metering apparatus 100. More specifically, several individual doses of a suspension of medicament and a suspending agent (2.5% weight/volume fluticasone propionate in a blend of 70% by volume PFMCH and 30% by volume hexane) were applied to SS carrier screens (FIG. 4) or to ETFE carrier screens (FIG. 5) using inventive metering apparatus 100, followed by evaporation of the agent, which is described in more detail below.

Detailed Description of Examples of Dosing Medicaments with Novel Metering Apparatus A 2.5% weight/volume suspension (of fluticasone propionate as the medicament and a blend of hexane with PFMCH as the suspending agent) was prepared as follows. Fluticasone propionate (375.04 mg) was weighed into a 7 dram (20 ml) scintillation vial using a calibrated balance (model no. UMT2 available from Mettler Instrument Corporation, Hightstown, N.J., USA) capable of 0.1 µg readability. The suspension media was prepared by adding 15 ml hexane to 35 ml PFMCH using graduated cylinders. The suspension media was allowed to warm to room temperature and was well mixed. Using a graduated cylinder, 15 ml of the suspension media was measured out and added to the scintillation vial. The resultant was shaken briefly and then sonicated in a bench top sonicator (model no. 5200 available from Branson Cleaning Company, Shelton, Conn., USA) for 1 minute to produce a finely admixed suspension.

Using a syringe, the suspension was filtered directly into a 2.5 ounce (0.083 liter) polyethylene reservoir through a small piece of 400 mesh stainless steel screen (hereinafter, abbreviated SS screen) to remove any foreign material that was possibly present. Once the suspension was added to the reservoir, the stirring rate was adjusted to a gentle, consistent speed that was visually confirmed prior to attaching the reservoir cap.

Nitrogen was supplied from a tank through a 3-way valve (part no. 86777, HVP3-3, available from Hamilton Company, Reno, Nev., USA) via respective tubes to either the reservoir or to a concentric nozzle. Nitrogen pressure to the reservoir was controlled through a regulator (part no. E3.UPE3150 580, available from Linde (currently, known as Praxair Distribution Inc., San Ramon, Calif., USA) and further reduced to 15 psig with a regulator (model no. 2002A, available from EFD, East Providence, R.I., USA). Fine adjustment of the nitrogen gas flow through the concentric nozzle was controlled using a gas valve (part no. 5S-21RS4 available from Whitey Company, Cleveland, Ohio, USA) and an uncalibrated flow meter (model no. 12, available from Gilmont Industries, Barrington, Ill., USA) that allowed the flow to be monitored up to 2000 ml/minute.

The reservoir was composed of a retainer body and cap assembly (part no. 5190R available from EFD, East Providence, R.I., USA) and a 2.5 ounce (0.083 liter) high density polyethylene cartridge (catalogue no. 5190C-SHD, available from EFD, East Providence, R.I., USA). The cap or top of the reservoir was modified to accept a drying tube filled with indicating anhydrous calcium sulfate (available under the registered trademark DRIERITE® (owned by W.A. Hammond Drierite Company, LTD, Xenia, Ohio, USA) as a desiccant. Although this modification allowed the suspension media to evaporate at an uncontrolled rate, the results indicated below showed that this was not a significant effect. The laboratory room temperature was maintained between 200 to 24° C., which further minimized the evaporation.

The suspension was stirred using a "S/P" football shaped magnetic stirring rod (part no. S8311-721x1/2 available from Baxter Diagnostics Inc., Scientific Products Division, McGraw Park, Ill., USA) and a magnetic stirring apparatus (part no. 11-498-78 available from Fisher Scientific International, Inc., Hampton, N.H., USA) placed on its side with the motor axis of the magnetic stirring apparatus parallel to the horizon and carefully positioned to provide maximum magnetic coupling. A slow stirring rate was utilized to ensure a homogenous suspension while minimizing concentration changes due to wall losses from suspension splashing.

A 5.5 inch (14 cm) length of tubing (available under the registered trademark TEFZEL from Optimize Technologies, Inc. Portland, Oreg., USA, with 0.0625 inch, i.e., 0.1588 cm, outer diameter and 0.03 inch, i.e., 0.0762 cm, inside diameter) was used as the outlet line to connect the reservoir to the pump (item no. QC 72, with pump-head/piston/liner assembly RHOOCKCLF including a suitable dial for setting the stroke volume of the pump piston, available from FMI (Fluid Metering Incorporated, Oyster Bay, N.Y., USA) ) via the tubing passing through a liquid junction container (described in the next paragraph below). A second 3-way valve (part no. 86777, HVP3-3 available from Hamilton Company, Reno, Nev., USA)) was used to divert the suspension flow from the reservoir to waste or to the pump. The ceramic piston and liner of the pump were manufactured with the standard clearance of 100 millionths of an inch.

A liquid junction container was formed from a trimmed-down high density polyethylene cartridge (available from EFD, East Providence, R.I., USA) and the outlet line tubing was passed through the container. The container was filled with water as liquid, so that the water surrounded the outlet line tubing. A sonic dismembrator (model no. 550 available from Fisher Scientific International, Inc., Hampton, N.H., USA) sonicator was positioned with its probe end in the water in order to provide mechanical vibrations at 20 KHz into the water. Thus, the sonicator was coupled to the outlet line tubing via the water.

The main body of the concentric nozzle was constructed using a 1.962 inch (9.78 cm) length of 0.010 inch (0.0254 cm) inner diameter×0.0625 inch (0.1588 cm) outer diameter HPLC (high pressure/liquid chromatography) stainless steel tubing of which one end was bored-out to 0.020 inch (0.051 cm). The nozzle tip was formed by removing the 0.01 inch (0.25 cm) inner diameter×0.099 inch (0.251 cm) outer diameter stainless steel tip from a nozzle (part no. 5125-B available from EFD, East Providence, R.I., USA). The nozzle tip was inserted into the bored HPLC tubing hole and firmly attached using cyanoacrylic glue.

The air sheath assembly of the concentric nozzle was constructed from brass tubing. The assembly was formed by inserting a 0.047 inch (0.119 cm) inner diameter x 0.061 inch (0.155 cm) outer diameter tube (the air sheath tube) into a 0.062 inch (0.157 cm) inner diameter×0.078 inch (0.198 cm) outer diameter coupling tube, so that the air sheath tube projected 0.511 inch (1.30 cm) from the coupling tube. For strength, the air sheath assembly was soldered together.

A nitrogen gas purge inlet line leading to the air sheath was formed from a 1.912 inch (4.856 cm) long piece of 0.036 inch (0.091 cm) inner diameter×0.061 inch outer diameter tubing. In the initial design of the concentric nozzle, the gas purge tube introduced nitrogen to the concentric nozzle at about a 300 angle; however, the air flow characteristics were found to be less than desired and hence the gas purge tube was repositioned at an angle of 90° to the nozzle tip. A small ribbon of polytetrafluoroethylene tape, 0.003 inch×0.25 inch×0.30 inch (0.007 cm×0.64 cm×0.76 cm), was wrapped around the 0.0625 inch (0.1588 cm) stainless steel tubing as a sleeve or jacket to ensure an air tight fit of the air sheath over the nozzle while still allowing for adjustments thereof.

Two different kinds of mesh screen carriers were employed. The first kind was a 400 mesh screen of stainless steel (hereinafter abbreviated as SS), with 38 $\mu$m holes and 36% open area. The second kind was a 169 mesh screen of ethylene tetrafluoroethylene copolymer (hereinafter, abbreviated as ETFE), with 70 $\mu$m holes and 22% open area. The SS carrier screen and the ETFE carrier screen are each the type of carrier screens as described above vis-a-vis U.S. Pat. No. 5,503,869 and U.S. patent application Ser. No. 08/328, 578.

Both the SS screen material and the ETFE screen material were obtained in 48 inch wide roles from which carrier screen strips approximately 0.8 inch×3.2 inches (2.0 cm×8.1 cm) were cut. All screens were cleaned to remove residual manufacturing oils by first washing the screens with hexane, followed by an acetone rinse. The carrier screens were then allowed to dry.

In order to keep each carrier screen in place during filling of the carrier screens with the suspension using the above-described metering apparatus having a reservoir, a liquid junction container, an out et line, a sonicator, a concentric nozzle, and a pump, the following holders and stages were employed. Each carrier screen was first placed in a screen-holder (6 carrier screens/holder). Then, the combination screen and screen-holder assembly was set in an x-y horizontal stage that was attached to a z-axis vertical stage (model 5000 available from Sherline Products, inc., San Marcos, Calif., USA), which for added stability, had been mounted to a base (part no. 6100 available from Sherline Products, Inc., San Marcos, Calif., USA). This allowed for accurate control of the horizontal and vertical positions of the assembly during metering with the apparatus. Each assembly of screen and screen-holder contained 6 patient doses (also referred to as drug dots) per screen and provided sufficient samples for determination of filling uniformity.

Using the metering apparatus, selected amounts of suspension were metered onto the carrier screens in a well controlled manner. The exact volume to be metered per dot was determined by estimating the correct dispensing volume from a pre-determined calibration curve, followed by dispensing the medicament onto the carrier screen and then assaying the dispersed dose. The dispensing volume was readjusted as indicated by the assay results and the dispersing dose checked again.

Sufficient assemblies of screen and screen-holder had been prepared to allow 3 trial loadings, and hence, during the first 3 loadings, the metering volume was adjusted so that thereafter a selected amount of suspension containing a target amount of 50 µg±5 µg of fluticasone propionate was dispensed per each of the 6 dose regions. In accordance therewith, the metering apparatus was initially adjusted to dispense approximately 2 µl of the 2.5% weight/volume suspension for each dose region. The same filling process used for the SS carrier screens was employed for the ETFE carrier screens, except as follows.

While the SS carrier screens were filled with 1 dispensing of approximately 2 µl per each of the 6 dosing regions, because of different surface characteristics, such as lower surface energy and mesh size differences, 2 µl of suspension, when applied to the ETFE carrier screens, produced unacceptably large drug dots which were approximately twice the size of the dots observed on the SS carrier screens. Thus, in this manner, the ETFE carrier screens were successfully filled with a target dose of 50 µg of fluticasone propionate per each of the 6 close regions by dispensing 2 aliquots of approximately equal but smaller volume of approximately 1 µl, instead of the 1 aliquot of approximately 2 µl volume as used for dispensing onto the SS screens.

The dial setting for the stroke volume of the pump piston utilized during the SS carrier screen filling was 2.75 per dispensing, which is equivalent to approximately 1.91 µl for each dot. The expected fluticasone propionate dispensed at this setting was 52.2 µg based on the calibration curve determined by high pressure liquid chromatography analysis. The dial setting for the stroke volume of the pump piston utilized during the ETFE carrier screen filling was 0.75 per 2 dispensings, which is equivalent to 1.66 µl for each dot. The expected fluticasone propionate dispensed at this setting was 46.2 µg based on the calibration curve determined by high pressure liquid chromatography analysis. Actual fluticasone propionate dispensed averaged 49.5 µg.

The dead volume of the outlet tube from the reservoir to the pump was calculated to be approximately 64 µl. To ensure complete purging of the outlet tube with uniform suspension, first approximately 191 µl of suspension was dispensed to waste. Hence, a total of approximately 100 dispensings were sent to waste prior to screen filling.

Next, a first set of 12 SS carrier screens plus 1 spare screen were filled with suspension, followed by filling a second set of 12 SS carrier screens.

The intended filling procedure was to maintain the tip to screen gap distance at about 0.005 inch±0.002 inch (0.013 cm±0.005 cm), and a gap of at least 0.001 inch (0.00254 cm) between the carrier screen and the nozzle tip was maintained.

After application of the suspension to the carrier screens, the suspending agent was allowed to evaporate at ambient conditions, and the carrier screens now loaded with fluticasone propionate were then assembled in the twin screen configuration, using 250 mesh SS top impaction screens with 63 µm holes and 36% open area, which are the type of impaction screens for the twin screen mode that is described above for U.S. Pat. No. 5,503,869 and U.S. patent application Ser. No. 08/328,578. Prior to assembly in the twin screen mode, the SS impaction screens were cleaned as described above vis-a-vis the carrier screens.

A representative screen from approximately the beginning, the middle, and the end of the filling campaign were assayed for medicament content using high pressure liquid chromatography. The loading and operating parameters are summarized in Tables A and B below:

TABLE A

Raw Material Lot Numbers and Sources

| Product Lot # | Fluticasone Propionate Lot # | Screen Roll # Source: Tetko, Inc., Braircliff Manor, New York, USA | Mesh Size* (carrier or impaction) |
| --- | --- | --- | --- |
| PFDD003 | ACN 65148 Lot #13 | B927195/15 B927138/32 | 400 (carrier) 250 (impaction) |
| PFDD004 | ACN 65148 Lot #13 | 16877020132 B927138132 | 169 (carrier) 250 (impaction) |

| Product Lot # | Screen Material | Wire Diameter* (inches) | PFMCH Lot # (Source: Fluorochem Ltd. Old Glossop, Derbyshire, United Kingdom) | Hexane Lot # (Source: Burdick & Jackson Div., Muskegon, Michigan, USA) |
| --- | --- | --- | --- | --- |
| PFDD003 | SS SS | 0.0010 0.0014 | 0048A | B6647 |
| PFDD004 | ETFE SS | 0.0031 0.0014 | 0048A | B6647 |

*Nominal values provided by supplier.

TABLE B

Filling Parameters

NOZZLE

| | |
| --- | --- |
| Air Sheath Flow | 900 ml/minute |
| Air Sheath Flow Gas | N2 (dry) |
| Mesh to Nozzle Tip Clearance | 0.005 in. (attempted) |
| Air Sheath to Nozzle Tip Clearance | 3.4 mm |
| Nozzle Inside Diameter | 0.01 in. |
| Sonication Power | 5 to 7% |

DISPENSING PUMP DIAL SETTING FOR STROKE VOLUME OF PUMP PISTON

| | |
| --- | --- |
| ETFE Carrier Screens | 0.75 × 2 |
| SS Carrier Screens | 2.75 |

As can be seen from the consistency of the results illustrated in the graphs in FIG. 4 (SS carrier screens) and FIG. 5 (ETFE carrier screens), the concentric nozzle of the metering apparatus was shown to be capable of dispensing fluticasone propionate from a suspension thereof with a standard deviation of the expected medicament dose on the order of 6%±1%.

It will be understood that various details of the invention may be changed without departing from the scope of the invention. Furthermore, the foregoing description is for the purpose of illustration only, and not for the purpose of limitation—the invention being defined by the claims.

What is claimed is:

1. An apparatus for applying to a carrier a suspension comprising a suspending agent and one or more doses of a powdered medicament, said apparatus comprising:

(a) a reservoir adapted to maintain the suspending agent and the powdered medicament in suspension, (b) an outlet line in fluid communication with the reservoir and extending from the reservoir to allow the suspension to travel by way of the outlet line;

(c) a concentric nozzle having a top and a bottom and formed from an inner cylinder disposed within an outer cylinder, thereby defining a space therebetween, and the inner cylinder terminating in a tip disposed adjacent the nozzle bottom, and further including a purge line fluidly connected with the outer cylinder for providing a gas jet to the space; and (d) a pump having a fluid inlet and a fluid outlet and fluidly connected at the fluid inlet to the outlet line and fluidly connected at the fluid outlet to the nozzle;

whereby, when the suspension travels from the outlet line to the pump and fills the pump with a selected amount of the suspension, the pump expels the selected amount of the suspension through the nozzle to the carrier.

2. The apparatus according to claim 1, wherein the suspending agent is selected from organic agents, inorganic agents, and combinations thereof.

3. The apparatus according to claim 2, wherein the organic suspending agents are selected from the group consisting of fluorinated hydrocarbons, chlorinated hydrocarbons, hydrocarbons, and combinations thereof.

4. The apparatus according to claim 2, wherein the inorganic suspending agents are selected from the group consisting of carbon dioxide, sulfur hexafluoride, and combinations thereof.

5. The apparatus according to any of claims 1–4, wherein the powdered medicament comprises a respirable medicament for inhalation therapy or systemic absorption via the respiratory tract to treat respiratory disorders such as asthma, bronchitis, chronic obstructive pulmonary diseases and chest infection.

6. The apparatus according to claim 5 wherein the powdered medicament comprises analgesics, anginal preparations, antiallergics, antiinfectives, antihistamines, anti-inflammatories, antitussives, bronchodilators, diuretics, anticholinergics, hormones, xanthines or therapeutic proteins or peptides, or combinations thereof.

7. The apparatus according to claim 6, wherein the powdered medicament comprises acetonide, adrenaline, albuterol, amiloride, aminophylline, atropine, bambuterol, beclomethasone, beclomethasone dipropionate, budesonide, cephalosporins, choline theophyllinate, codeine, cortisone, cromoglycate, dihydromorphine, diltiazem, disodium cromoglycate, ephedrine, ergotamine, fenoterol, fentanyl, flunisolide, fluticasone, fluticasone propionate, formoterol, glucagon, hydrocortisone, insulin, ipratropium, isoetharine, isoprenaline, isoproterenol, ketotifen, lysine theophyllinate, metaproterenol, methapyrilene, mometasone, morphine, neodocromil, noscapine, orciprenaline, oxitropium, penicillins, pentamidine, phenylephrine, phenylpropanolamine, pirbuterol, prednisolone, reproterol, rimiterol, salmbutamol, salmeterol, stretomycin, sulphonamides, tetracyclines, theophylline, tipredane, triacetonide, triamcinolone acetonide, terbutaline, tulobuterol, terbutaline, tulobuterol, (−)-4-amino-3,5-dichloro-α-[[[6-[2-(2-pyridinyl)ethoxy]hexyl]amino]methyl]benzenemethanol, pharmaceutically acceptable salts and esters thereof, and combinations thereof.

8. The apparatus according to any of claims 1 to 7, wherein the gas jet is provided continuously from the purge line.

9. The apparatus according to any of claims 1 to 8, wherein the gas jet provided from the purge line will prevent capillary forces from allowing the selected amount of the suspension, as it is expelled, from collecting around the tip of the inner cylinder of the nozzle.

10. The apparatus according to any of claims 1 to 9, wherein the reservoir has an agitator device associated therewith, for maintaining the suspending agent and the powdered medicament mixture as the suspension.

11. The apparatus according to claim 10, wherein the agitator device is selected from the group consisting of a mechanical stirring apparatus, a magnetic stirring apparatus, and combinations thereof.

12. The apparatus according to claim 11, wherein the reservoir has a magnetic stirring apparatus located proximate thereto and the suspension has a magnetic stirring rod placed therein, for maintaining the suspending agent and the powdered medicament mixture as the suspension.

13. The apparatus according to any of claims 1 to 12, wherein the reservoir has fluidly connected therewith a gas line adapted for providing a gas blanket in the reservoir on top of the suspension.

14. The apparatus according to any of claims 1 to 13, wherein the reservoir has fluidly connected therewith a drying tube containing a desiccant for preventing moisture from being inside the reservoir.

15. The apparatus according to any of claims 1 to 14, wherein the tip of the inner cylinder has an inside diameter from about 0.010 inch to about 0.035 inch.

16. The apparatus according to claim 15, wherein the tip of the inner cylinder has an inside diameter from about 0.016 inch to about 0.030 inch.

17. The apparatus according to any of claims 1 to 16, wherein the tip of one or both of the inner cylinder and the outer cylinder is adjustable in position.

18. The apparatus according to any of claims 1 to 18, wherein the tip of the inner cylinder is extended beyond the tip of the outer cylinder.

19. The apparatus according to any of claim 1 to 18, wherein the pump includes a piston that fills with the selected amount of the suspension.

20. The apparatus of any claims 1 to 19, wherein for expelling the selected amount of the suspension, the pump is adapted to provide one stroke to the piston concurrently with the purge line providing the gas jet.

21. The apparatus according to any of claims 1 to 20, wherein the selected amount of the suspension contains a quantity of the powdered medicament that is selected from the group consisting of one dose, more than one dose, and less than one dose.

22. The apparatus according to any of claims 1 to 21, the apparatus further including a positioning system to maintain in place at least one of the apparatus and the carrier so that the apparatus is properly aligned over the carrier as the suspension is expelled through the nozzle to the carrier.

23. The apparatus according to any of claims 1 to 22, wherein the apparatus further includes:

(e) a junction container adapted to contain a liquid so that the outlet line extends from the reservoir through the junction container to allow the suspension to travel by way of the outlet line through the junction container; and (f) a sonicator operatively associated with the junction container to agitate a liquid in contact with the outlet line so that the pump is fluidly connected at the fluid inlet to the outlet line after the outlet line exits the junction container.

24. An apparatus adapted for applying to a carrier a suspension comprising a suspending agent and one or more doses of a powdered medicament, said apparatus comprising:

(a) a reservoir adapted for maintaining the suspending agent and the powdered medicament admixed in suspension, wherein the reservoir has fluidly connected therewith (i) a gas line adapted for providing a gas blanket in the reservoir on top of the suspension and (ii) a drying tube containing a desiccant for preventing moisture inside the reservoir;

(b) a magnetic stirring apparatus located proximate to the reservoir and an associated magnetic stirring rod placed in the suspension, for maintaining the suspending agent and the powdered medicament admixed as the suspension;

(c) a junction container adapted to contain a liquid;

(d) an outlet line in fluid communication with the reservoir and extending from the reservoir through the junction container to allow the suspension to travel by way of the outlet line through the junction container;

(e) a sonicator operatively associated with the junction container to agitate a liquid in contact with the outlet line and thereby preventing the suspension traveling through the outlet line from forming floccules;

(f) a concentric nozzle having a top and a bottom and formed from an inner cylinder disposed within an outer cylinder, thereby defining a space therebetween, and the inner cylinder terminating in a tip extending beyond the nozzle bottom, and including a purge line fluidly connected with the outer cylinder for providing a gas jet to the space; and (g) a pump having a piston and an associated cylinder, and having a fluid inlet and a fluid outlet, the piston being adapted both for rotating and for moving longitudinally, the pump being fluidly connected at the fluid inlet to the outlet line where the outlet line exits the junction container and fluidly connected at the fluid outlet to the nozzle, so that via the piston rotating, the suspension may travel from the cutlet line where the outlet line exits the junction container and into the piston cylinder wherein the piston cylinder will be filled with a selected amount of the suspension; whereby a stroke of the piston by the pump expels the selected amount of the suspension out of the piston cylinder and through the inner cylinder to such a carrier and a gas jet from the purge line concurrently provided with the stroke of the pump prevents capillary forces from allowing the selected amount of the suspension, as it is expelled, from collecting around the tip of the inner cylinder of the nozzle.

25. The apparatus according to claim 24, wherein the suspending agent is selected from organic agents, inorganic agents, and combinations thereof.

26. The apparatus according to claim 25, wherein the organic suspending agents are selected from the group consisting of fluorinated hydrocarbons, chlorinated hydrocarbons, hydrocarbons, and combinations thereof.

27. The apparatus according to claim 25, wherein the inorganic suspending agents are selected from the group consisting of carbon dioxide, sulfur hexafluoride, and combinations thereof.

28. The apparatus according to any of claims 24 to 27, wherein the powdered medicament is selected from the group consisting of acetonide, adrenaline, albuterol, amiloride, aminophylline, atropine, bambuterol, beclomethasone, beclomethasone dipropionate, budesonide, cephalosporins, choline theophyllinate, codeine, cortisone, cromoglycate, dihydromorphine, diltiazem, disodium cromoglycate, ephedrine, ergotamine, fenoterol, fentanyl, flunisolide, fluticasone, fluticasone propionate, formoterol, glucagon, hydrocortisone, insulin, ipratropium, isoetharine, isoprenaline, isoproterenol, ketotifen, lysine theophyllinate, metaproterenol, methapyrilene, mometasone, morphine, neodocromil, noscapine, orciprenaline, oxitropium, penicillins, pentamidine, phenylephrine, phenylpropanolamine, pirbuterol, prednisolone, reproterol, rimiterol, salmbutamol, salmeterol, stretomycin, sulphonamides, tetracyclines, theophylline, tipredane, triacetonide, triamcinolone acetonide, terbutaline, tulobuterol, terbutaline, tulobuterol, (−)-4-amino-3,5-dichloro-a-[[[6-[2-(2-pyridinyl)ethoxy]hexyl]amino] methyl]benzenemethanol, pharmaceutically acceptable salts and esters thereof, and combinations thereof.

29. The apparatus according to any of claims 24 to 28, wherein the tip of the inner cylinder has an inside diameter from about 0.010 inch to about 0.035 inch.

30. An apparatus adapted for applying to a carrier a suspension comprising a suspending agent and at least one dose of a powdered medicament, after which the suspending agent is evaporated off leaving the powdered medicament applied to the carrier, said apparatus comprising:

(a) a reservoir adapted to maintain the suspending agent and the powdered medicament admixed in suspension;

(b) a junction container adapted to contain a liquid;

(c) an outlet line in fluid communication with the reservoir and extending from the reservoir through the junction container to allow such a suspension to travel by way of the outlet line through the junction container;

(d) a sonicator operatively associated with the junction container to agitate a liquid in contact with the outlet line and thereby to prevent the suspension traveling through the outlet line from agglomerating into floccules;

(e) a concentric nozzle having a top and a bottom and formed from an inner cylinder disposed within an outer cylinder, thereby defining a space therebetween, and the inner cylinder terminating in a tip disposed adjacent the nozzle bottom, and further including a purge line fluidly connected with the outer cylinder for providing a gas jet to the space; and (f) a pump having a fluid inlet and a fluid outlet and fluidly connected at the fluid inlet to the outlet line from the junction container and fluidly connected at the fluid outlet to the nozzle, so that the suspension may travel from the outlet line, to the pump and fill the pump with a selected amount of suspension;

whereby the pump will expel the selected amount of the suspension through the nozzle to the carrier and a gas jet provided from the purge line prevents capillary forces from allowing the selected amount of the suspension, as it is expelled, from collecting around the tip of the inner cylinder of the nozzle.

* * * * *